(12) United States Patent
Josefsson

(10) Patent No.: US 6,415,043 B1
(45) Date of Patent: Jul. 2, 2002

(54) METHOD AND ARRANGEMENT FOR DETERMINING THE POSITION OF AN OBJECT

(75) Inventor: Thorleif Josefsson, Partille (SE)

(73) Assignee: Qualisys AB (SE)

( * ) Notice: Subject to any disclaimer, the term of this patent is extended or adjusted under 35 U.S.C. 154(b) by 0 days.

(21) Appl. No.: 09/350,883

(22) Filed: Jul. 9, 1999

Related U.S. Application Data

(63) Continuation of application No. PCT/SE98/00033, filed on Jan. 13, 1998.

(30) Foreign Application Priority Data

Jan. 13, 1997 (SE) ................................................ 9700066

(51) Int. Cl.[7] .................................................. G06K 9/00
(52) U.S. Cl. ........................ 382/103; 348/141; 382/291
(58) Field of Search ................................. 382/291, 117, 382/100, 103, 107, 199, 203, 218, 219, 286, 300, 312; 345/641, 7; 348/135, 172, 157, 141; 250/221; 396/51, 89

(56) References Cited

U.S. PATENT DOCUMENTS

| | | | |
|---|---|---|---|
| 4,513,438 A | * 4/1985 | Graham et al. | 382/291 |
| 5,072,294 A | 12/1991 | Engle | 348/172 |
| 5,231,674 A | 7/1993 | Cleveland | 382/117 |
| 5,291,564 A | * 3/1994 | Shah et al. | 382/291 |
| 5,323,470 A | * 6/1994 | Kara et al. | 382/103 |
| 5,459,793 A | 10/1995 | Naoi | 382/165 |
| 5,481,620 A | * 1/1996 | Vaidyanathan | 382/291 |
| 5,499,306 A | * 3/1996 | Sasaki et al. | 382/291 |
| 5,604,820 A | * 2/1997 | Ono | 382/291 |

OTHER PUBLICATIONS

International Search Report; International Application No. PCT/SE 98/00033; Apr. 1, 1998.
International Preliminary Examination Report, International Application No. PCT/SE98/00033; International Filing Date: Jan. 13, 1998.

* cited by examiner

Primary Examiner—Jayanti K. Patel
(74) Attorney, Agent, or Firm—Lerner, David, Littenberg, Krumholz & Mentlik, LLP

(57) ABSTRACT

A method for determining a position of a body having at least one marker object with a known dimension parameter. The method utilizes at least one camera unit having a sensor device and an optical element a determinable distance from the sensor device. The at least one camera unit includes an element for retrieving and calculation. The method includes the steps of computing the coordinates of an image of the object reproduced on the sensor device, computing a dimension parameter of the object corresponding to the known dimension parameter of the at least one marker object and calculating the proportion of parameters obtained to determine the position of the object.

11 Claims, 2 Drawing Sheets

METHOD AND ARRANGEMENT FOR DETERMINING THE POSITION OF AN OBJECT

CROSS-REFERENCE TO RELATED APPLICATIONS

This is a continuation of International Application No. PCT/SE98/00033 filed on Jan. 13, 1998.

TECHNICAL FIELD OF THE INVENTION

The present invention relates to a method and arrangement for determining position of a body provided with at least one marker object with a known dimension parameter, by means of at least one camera unit, provided with a sensor device and an optical element in a determinable distance from said sensor device, and means for retrieving and calculation.

BACKGROUND AND RELATED ART

Motion analysis is now a well-known method using camera unit and computer aid to analyse, e.g. biomechanichs of human, animals or motions of a robot arm etc.

In a simple system markers are attached to the object to be analysed. In the past the object provided with the markers was first filmed and then manually analysed and digitalised to determine the correct position of the markers. This was a time-consuming procedure.

Presently, cameras equipped with so-called CCD plates are used. CCD plate, which is a light sensor, is generally arranged in communication with necessary optical elements. A CCD plate, consisting of lines of charged coupled sensors arranged as a matrix, i.e. arranged in an X and Y coordinate system, for one or several colours, converts the light (from the optical element) projected on it, by electronically scanning in Y direction each line of X sensors and producing a television (video) signal. Then, the signals may be analysed in different ways to detect the position of the markers attached to the object.

Presently, two or more camera units are used to measure the distance to an object.

SUMMARY OF THE INVENTION

It is an object of the present invention to present a method and device to accurately determine the position, preferably the three dimensional position of an object using at least one camera unit, substantially in real time.

These objects are achieved by using a method, comprising steps of:
computing the coordinates of an image of said object reproduced on said sensor device,
computing a dimension parameter of said object corresponding to said provided dimension parameter,
calculating the proportion of parameters obtained to determine the position of said object.

The invention also concerns an arrangement for determining the position of a body provided with an object having a known dimension parameter to said body, said system comprising at least one camera unit, including a sensor device and an optical element, in a determinable distance from said sensor device, and means for retrieving and calculation, which is arranged to compute the coordinates of an image of said object reproduced on said sensor device, compute a dimension parameter of said object corresponding to said provided dimension parameter, calculate the proportion of parameters obtained to determine the position of said object and means for presenting the determined position.

Other advantageous embodiment according to the present invention are characterised in depending claims.

BRIEF DESCRIPTION OF THE DRAWINGS

In the following the invention will be described with reference to enclosed drawings, in, which.

BASIC THEORY

Figure 1:
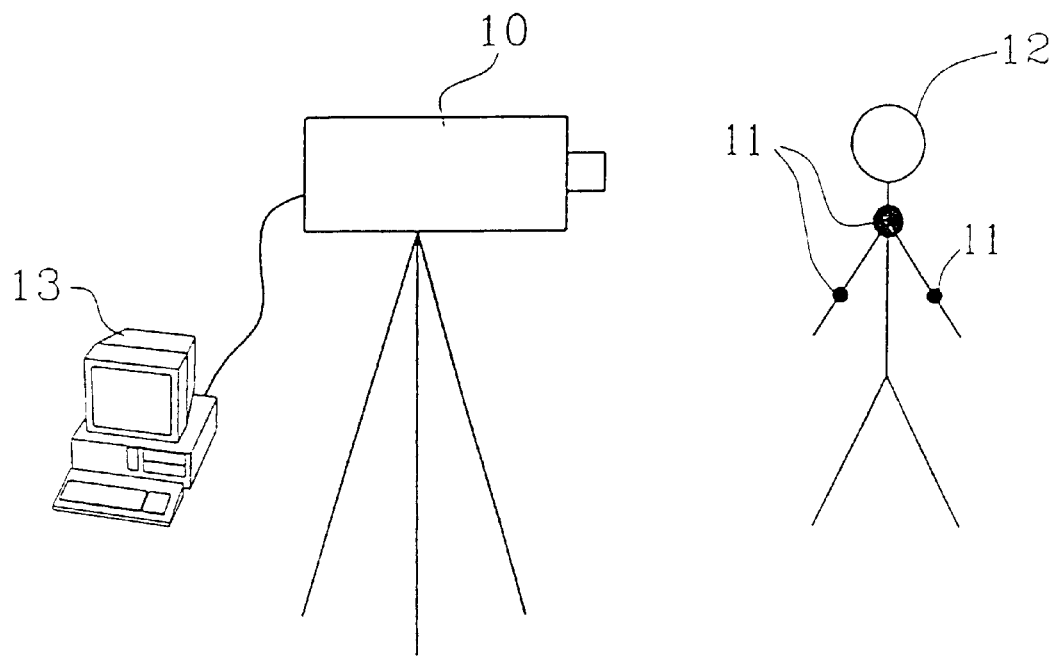
FIG. 1 is a schematic diagram of a simple motion analyse system according to the invention.

Basically, an analogous system uses a conventional video signal from a camera as an input. By means of said signal the X and Y coordinates for the marker, which separate from the surroundings in intensity of light are calculated. The aim is to measure a movement of the marker as exact as possible, i.e. the inaccuracy, which is a result of the video signal consisting of a set of finite number of dots to be minimised.

The video signal consists of a number of lines, which are scanned in chronological order. A marker generates an image, which extends over one or several lines. By means of a comparator, it is possible to determine the start and the end of a marker section on a line may be determined. The marker image on a line is called a segment. The time is measured partly from the beginning of the line to the beginning of the segment ($X_s$) and partly from the beginning of the line to the end of the segment ($X_e$). The mean value of these two periods is a measure for the position of a segment in the space, in horizontal direction (if the lines are horizontal) while the serial number of the line (S) is a measure for position of the segment in the vertical direction. The length l of the segments is then $X_e - X_s$.

The X and Y coordinates of the marker, $X_m$ and $Y_m$, respectively are obtained through formulas 1 and 2:

$$X_m = \frac{\sum \frac{(X_e - X_s) \cdot (X_e + X_s)}{2}}{\sum (x_e - X_s)} \quad (1)$$

$$Y_m = \frac{\sum ((X_e - X_s) \cdot S)}{\sum (x_e - X_s)} \quad (2)$$

The Σ sign indicates that the summation is carried out over all segments being a member of the marker image.

The above is applicable for an analogous signal. Similar calculations may be carried out, if image dots from a digital detector are transferred to another order than linear, where the centre points for all image elements that are members of the same marker are calculated. First, the image elements can be translated to lines and then the calculation may be carried out as in the analogous case.

The times $X_s$ and $X_e$ can be measured with an electronic counting device connected to an oscillator, which also controls the video signal. The counter starts in the beginning of the line and it is read when the start and end of a segment are reached. One problem is that the oscillator frequency, due to technical and economical reasons is limited. In the digital case the problem may be that the image elements cannot be as small as required.

To overcome this problem in analogues case, a comparator is provided, which starts an integrator, which generates a linear potential slope, which starts from a potential $V_a$ to $V_b$ at time $X_s$. The slope is than sampled and measured when the counter changes between two values. The point when the slope passes a predetermined alteration value is used to define the time $X_{ss}$. The difference between $X_s$ and $X_{ss}$ is a constant and it is determined by the integrator and the delays in the comparators. The time $X_{ss}$ is easily calculated from the measured points on the potential slope at the time for the change of the counter provided that at least two points on the slope are measured. For example, if two voltage values are measured, $V_1$ at $t_1$ and $V_2$ at $t_2$ and $V_0$ is between $V_1$ and $V_2$, $X_{ss}$ is interpolated by formula 3:

$$X_{ss} = t_1 + \frac{(t_2 - t_1) \cdot (V_0 - V_1)}{V_2 - V_1} \quad (3)$$

The time $X_e$ is measured in same way. In this embodiment a linear slope is used, because the calculations become simpler, however, other curves may be used.

DETAILED DESCRIPTION OF AN EMBODIMENT

A simple schematic system according to the present invention is shown in FIG. 1. The system comprises at least one camera 10 directed to a body, in this case a human body 12, to be analysed and at least one marker is attached to the body 12.

The camera 12 may be connected to a computer device 13, to further process the received signals from the camera 10.

In the following, references will be made to an embodiment of a system operating in IR region, i.e. the camera "sees" bodies emitting infrared radiation. In a preferred embodiment the marker has a substantially spherical configuration provided with a reflecting surface. The camera 12 may be provided with means to emit IR-light, which is then reflected by the marker. The special design of the marker allows the cameras from different angels apprehend a circular form for a correct positioning.

Figure 2:
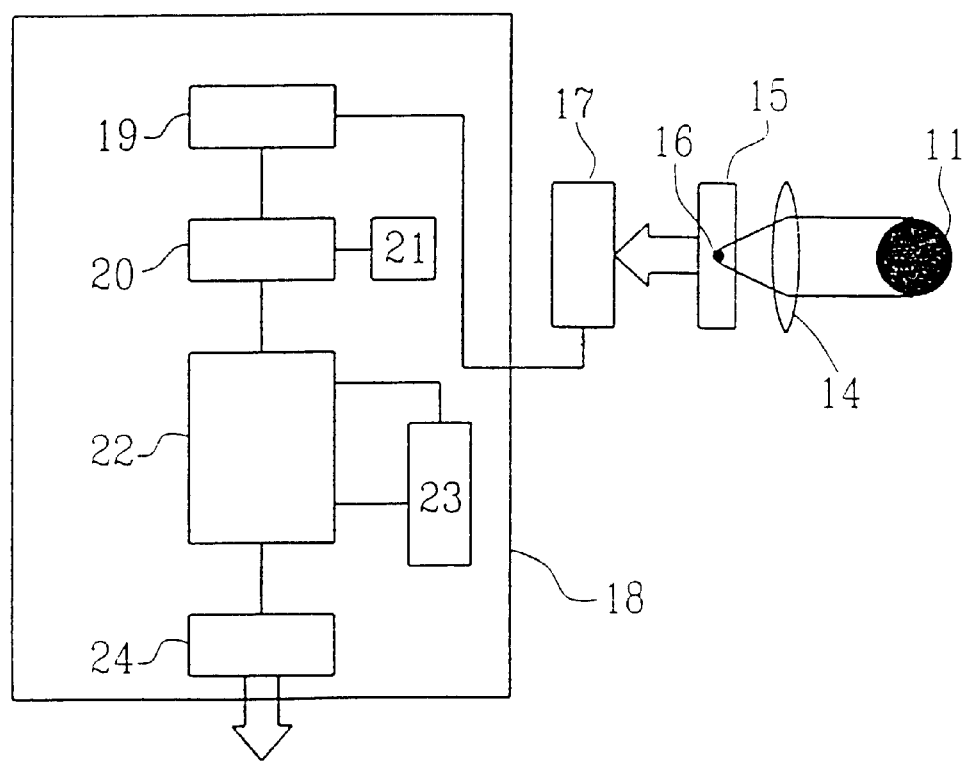
FIG. 2 is a schematic illustration of the camera according to FIG. 1.

In this embodiment the camera 10 is equipped with a CCD unit operating substantially in same way as described above. The block diagram of FIG. 2 schematically illustrates some primary parts of the camera 12 intended to execute the method according to the invention.

The camera 10 includes optical elements 14 such as lenses and other focusing means (not shown) to project the image 16 of a marking device 11 onto a CCD unit 15. The surface of the CCD unit is then scanned and the image signals including pixel information are converted to a suitable video signal by means of a converting unit 17, which may be integrated in the CCD unit. The video signal representing image lines, is then serially or in parallel sent to a processing unit 18. The processing unit digitalises the received video signal, for example using an A/D-converter 19. This signal may also be digitalised in unit 17. The processing unit may be connected to a memory unit, not shown, containing a set of instructions for controlling the processing unit.

In respect of the "Basic Theory" part, herein above, the image elements may be arranged in lines by means of a low-pass filter to provide some continues signal, which can be processed as the analogous signal. However, in the preferred embodiment each image element is measured individually and from the measured values, a value is interpolated, determining when a threshold T is passed, analogously to the Basic Theory part.

The digitalized signal is then passed over to a comparison unit 20, which interpolates individual sample values about the predetermined threshold value T, also called video level, which may be obtained from a memory unit 21. As described above, the object is to determine when the amplitude of the signal passes the value T. Each passage presents a start and stop coordinate of each segment with a high resolution, which can be about 30×number of pixels on a row. In a computation unit 22 following calculation is executed:

$$X_{high\ resolution} = \text{Pixel No.} + \frac{T - V_1}{V_2 - V_1} \quad (4)$$

Where $V_1$ and $V_2$ are the signal levels of preceding and succeeding pixels, respectively, received from the comparatione unit 21.

The pixel number may be obtained from a counter (not shown)

Depending on the components used, levels $V_1$ and $V_2$ may be measured having resolution of 10 bits, the pixel number (MSS) 9 bits and $(T-V_1)/(V_2-V_1)$ 7 bits. Then the centre point x' of the marker is computed in a computation unit 22 by means of previous values stored in a memory unit 23, using formula (5):

$$x' = \frac{\sum (l_k^n \cdot \bar{x}_k)}{\sum l_k^n} \quad (5)$$

$$y' = \frac{\sum (l_k^n \cdot S)}{\sum l_k^n} \quad (6)$$

where $l_k$ is the length of the segment k (i.e., $X_{ek}-X_{sk}$), according to FIG. 5, S is the serial number of the image element, and $x_k$ is the centre of the segment k.

In the digital case, the formulas (1) and (2) are substituted by formulas (5) and (6), respectively. However, formula (1) and (2) alone do not contribute to obtaining an exact value as desired. To obtain a more accurate, stable and high resolutive x', the n power of $l_k$ is calculated. In the preferred embodiment the square of $l_k$, i.e. n=2 is calculated.

Figure 3:
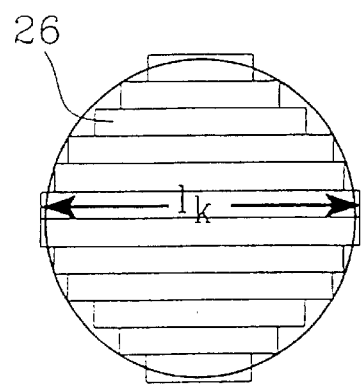
FIG. 3 is a schematic section through a digitalised marker according to the present invention.

FIG. 3 schematically illustrates the digitalized two dimensional image 26 of the marker.

The $l_k$'s may then be stored in the memory unit 23, for further calculations. For a circular marker, the area A of the image is calculated using formula $A \approx \Sigma l_k$. It is also possible to calculate the radius using $A \approx r^2 \cdot \pi$, which yields formula (7):

$$r = \sqrt{\frac{\Sigma l_k}{\pi}}, \quad (7)$$

which may be computed in the computation unit 22.

Figure 4:
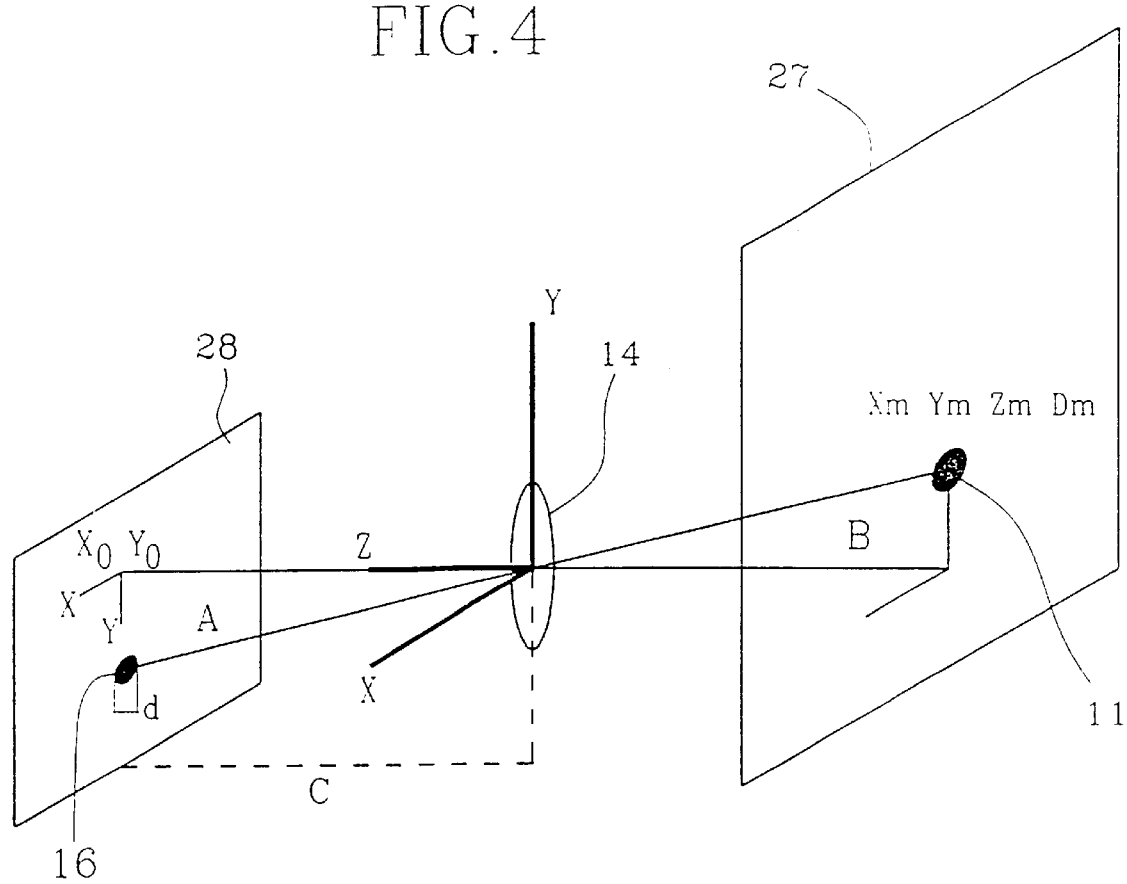
FIG. 4 schematically illustrates the principle of the present invention.

Referring now to FIG. 4, which schematically illustrates the fundamental principle of the present invention, the position of the object 11 may be calculated according to the following.

Following are known data:
  x' the centre of the marker image 26 on the detector plane 28, i.e. on the CCD plate 15, computed using formula 5;

c the distance c from the detector plane 28 to the lens 14;

$X_0, Y_0$ the centre of the detector plane, corresponding to the centre of the lens, which art camera constants;

$D_m$ the diameter of the marker 11.

In the calculation unit 22 following parameters are calculated:

$x_p$ $X_0-x'$, i.e. the X-coordinate of the marker image on the detector plane relative the centre of the detector plane;

$y_p$ $Y_0-y'$, i.e. the X-coordinate of the marker image on the detector plane relative the centre of the detector plane; and d r×2, r being the radius as above.

As between the triangle B and the triangle A in FIG. 4, similarity exists, following proportional relationship also exist: $X_m/x_p=Y_m/Y_p=Z_m/c=D_m/d$, which enables following calculations in the unit 22:

$$X_m = \frac{D_m}{d} \cdot x_p \quad (8)$$

$$Y_m = \frac{D_m}{d} \cdot y_p \quad (9)$$

$$Z_m = \frac{D_m}{d} \cdot c \quad (10)$$

Where $X_m, Y_m$ and $Z_m$ are the three-dimensional position (vector components) of the marker, and specially the distance between the camera (lens) and the object (11) is $$Dist = \sqrt{X_m^2 + Y_m^2 + Z_m^2} . \quad (11)$$

It is obvious that the distance c must be determined exactly as said distance varies when focusing, i.e. when said lens is displaced.

The results may then be transformed to an interface unit to further transmission to the computer unit 13, in which the computed values, can be used to show the position of the marker on a screen for simulation, positioning and other applications.

Although, we have described and shown a preferred embodiment, the invention is not limited to said embodiment, variations and modifications may be made within the scope of the attached claims. The processing unit 18 may be integrated in the camera 10, or in a peripheral unit. The number of units and their function in the processing unit 18 may also vary.

Further, the form of the marker may vary due to the application area. Moreover, the system according to the invention may be used to detect distances in other areas, for example in mobile units such as vehicles, aeroplanes etc.

List of Designation Signs

10 Camera unit
11 Marker
12 Body
13 Computer
14 Lens
15 CCD unit
16 Image
17 Converting unit
18 Processing unit
19 A/D-converting unit
20 Comparator
21 Memory unit
22 Calculation unit
23 Memory unit
24 Interface unit
25 Marker
26 Marker image
27 Measurement plane
28 Detector plane

What is claimed is:

1. A method for determining X, Y and Z-axis coordinates of a marker comprising:

placing said marker having a predetermined dimension on a body;

providing a camera including an optical element and an optical sensing device having a center point, said camera being adapted for projecting an image of said marker onto said optical sensing device, wherein a distance between said optical element and said optical sensing device is known;

projecting the image of said marker onto said optical sensing device;

determining the center point of said projected image relative to the center point of said optical sensing device, the center point of said projected image including both X and Y-axis coordinates relative to the center point of said optical sensing device;

determining a dimension parameter of the image projected onto said optical sensing device; and using the predetermined dimension parameter of said marker, the determined dimension parameter of said projected image, the determined center point of said projected image, and the known distance between said optical element and said optical sensing device to determine the X, Y, and Z-axis coordinates of said marker.

2. The method according to claim 1, wherein a distance to said object is determined using the proportionality between the distance to said object and the determinable distance between the optical element and sensor plane, and the dimension parameters of the image of the object on said sensor device and the dimension parameter of the object.

3. The method according to claim 1, wherein the center coordinate of said image is the distance between a center point of the image and a center point on said sensor device.

4. The method according to claim 3, further comprising the step of calculating the center point of said image on said sensor device the calculating step including the steps of interpolating a signal from the sensor device containing pixel data for the image of the object on the sensor device and calculating a center point for a length of a segment representing a section of said image; and using the calculated center point and the length of the segment to determine the centroid coordinate by using the formula:

$$\hat{y} = \frac{\sum (I_k^n \cdot S)}{\sum I_k^n},$$

-continued $$\bar{x} = \frac{\sum (l_k^n \cdot \bar{x}_k)}{\sum l_k^n}.$$

5. The method according to claim 3, wherein said start or end point ($x_k$) is calculated using the formula:

$$X_k = p_m + \frac{T - V_1}{V_2 - V_1}$$

Where T is a predetermined threshold value $V_1$ and $V_2$ are signal levels of preceding and succeeding pixels, respectively; and p is the number of the pixel m.

6. The method according to claim 1, further comprising the steps of:
   interpolating signal containing pixel data for said image and calculating a length of a segment representing a section of said image; and
   using the calculated length of the segment to determine the area (A) of the image using the formula $A = \Sigma l_k$.

7. The method according to claim 1, wherein said marking object is substantially spherical.

8. The method according to claim 1, wherein said known dimension parameter is the diameter of the object.

9. An arrangement for determining X, Y and Z-axis coordinates of a marker having a predetermined dimension said arrangement comprising:
   a camera including an optical element and an optical sensing device having a center point, the distance between said optical element and said optical sensing device being predetermined, wherein said camera is adapted for projecting an image of said marker onto said optical sensing device; and
   a processor for determining the center point of said projected image relative to the center point of said optical sensing device, the center point of said projected image including both X and Y-axis coordinates relative to the center point of said optical sensing device, determining a dimension parameter of the image projected onto said optical sensing device, wherein said processor uses the predetermined dimension parameter of said marker, the determined dimension parameter of said projected image, the determined center point of said projected image, and the known distance between said optical element and said optical sensing device for determining the X, Y, and Z-axis coordinates of said marker.

10. The arrangement according to claim 9, further comprising:
    means for collecting image data for said body;
    converting means for producing a digital signal containing pixel data for said reproduced image;
    a comparator unit for generating a difference between a pixel signal level and a threshold value;
    a computation unit for calculating a center point for a length of each segment representing a section of said image; and means for calculating a centroid coordinate and/or an area of said image and/or a radius of said image.

11. The arrangement according to claim 9, wherein said sensor device includes a CCD plate.

* * * * *

UNITED STATES PATENT AND TRADEMARK OFFICE
CERTIFICATE OF CORRECTION

PATENT NO. : 6,415,043 B1
DATED : July 2, 2002
INVENTOR(S) : Thorleif Josefsson

It is certified that error appears in the above-identified patent and that said Letters Patent is hereby corrected as shown below:

Column 1,
Line 11, "TECHNICAL FIELD OF THE INVENTION" should read
-- BACKGROUND OF THE INVENTION --.
Line 20, please delete "BACKGROUND AND RELATED ART".
Line 27, "digitalised" should read -- digitalized --.
Line 38, "analysed" should read -- analyzed --.

Column 2,
Line 11, "analyse" should read -- analyze --.
Lines 12-13, "illustration of the camera according to FIG. 1" should read -- diagram of a simple motion analyze system according to the invention according to FIG. 1 --.
Line 15, "digitalised" should read -- digitalized --.
Line 20, "BASIC THEORY" should read -- DETAILED DESCRIPTION --.
Line 28, "minimised" should read -- minimized --.
Line 59, "centre" should read -- center --.

Column 3,
Line 27, please delete "DETAILED DESCRIPTION OF AN EMBODIMENT".
Line 32, "analysed" should read -- analyzed --.
Line 60, "digitalises" should read -- digitalizes --.
Line 62, "digitalised" should read -- digitalized --.

Column 4,
Line 23, after "shown)" insert -- . --.
Line 26, "MSS" should read -- MSE --.

UNITED STATES PATENT AND TRADEMARK OFFICE
CERTIFICATE OF CORRECTION

PATENT NO. : 6,415,043 B1
DATED : July 2, 2002
INVENTOR(S) : Thorleif Josefsson

It is certified that error appears in the above-identified patent and that said Letters Patent is hereby corrected as shown below:

Column 5,
Line 3, "centre" should read -- center --.
Line 8, "centre" should read -- center --.
Line 14, "exists, following" should read -- exists, the following --.
Line 52, "aeroplanes" should read -- airplanes --.

Signed and Sealed this

Fourteenth Day of January, 2003

JAMES E. ROGAN
*Director of the United States Patent and Trademark Office*